US009816901B2

(12) United States Patent
Cacace

(10) Patent No.: US 9,816,901 B2
(45) Date of Patent: Nov. 14, 2017

(54) DISPOSABLE DIRECT CAPTURE DEVICE

(71) Applicant: EMD Millipore Corporation, Billerica, MA (US)

(72) Inventor: Benjamin Cacace, Tewksbury, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 14/438,961

(22) PCT Filed: Dec. 13, 2013

(86) PCT No.: PCT/US2013/074857
§ 371 (c)(1),
(2) Date: Apr. 28, 2015

(87) PCT Pub. No.: WO2014/120344
PCT Pub. Date: Aug. 7, 2014

(65) Prior Publication Data
US 2015/0292991 A1    Oct. 15, 2015

Related U.S. Application Data

(60) Provisional application No. 61/759,142, filed on Jan. 31, 2013.

(51) Int. Cl.
*G01N 30/00* (2006.01)
*B01L 3/00* (2006.01)
(Continued)

(52) U.S. Cl.
CPC .............. *G01N 1/34* (2013.01); *B01J 39/26* (2013.01); *B01J 41/20* (2013.01); *B01J 47/014* (2017.01);
(Continued)

(58) Field of Classification Search
CPC ............. G01N 30/00; G01N 2030/009; G01N 2030/0095; B01L 3/505; B01J 20/28023; B01J 20/28038
See application file for complete search history.

(56) References Cited

U.S. PATENT DOCUMENTS 4,119,267 A * 10/1978 Kydonieus ............. B65D 31/02
                                                        604/408
5,466,377 A    11/1995 Grandics et al.
(Continued)

FOREIGN PATENT DOCUMENTS

CN       2687112 Y      3/2005
CN       1950112 A      4/2007
(Continued)

OTHER PUBLICATIONS

International Preliminary Report on Patentability received for PCT Patent Application No. PCT/US2013/074857, dated Aug. 13, 2015, 12 pages.
(Continued)

*Primary Examiner* — Jan Ludlow
(74) *Attorney, Agent, or Firm* — EMD Millipore Corporation

(57) ABSTRACT

The invention relates to a liquid sample preparation device such as a disposable, collapsible, flexible polymeric bag containing an adsorptive curtain of a functionalized shaped polymeric fiber bed for the direct capture of biomolecules from liquid samples. The functionalized shaped polymeric fiber bed includes fibrillated, ridged or winged-shaped fiber structures that significantly increases the surface area of the fiber resulting in enhanced separation, retention and/or purification of liquid samples containing biomolecules of interest as the liquid samples contact the adsorptive curtain of functionalized shaped fibers. Liquid samples include unclarified liquid feeds or other liquids containing one or more biomolecules of interest, including, but not limited to vaccines, recombinant proteins, cells, stem cells, monoclonal antibodies (mAbs), proteins, antibody, peptides, oligopeptides, nucleic acids, oligonucleotides, RNA, DNA, oligosaccharides and polysaccharides.

11 Claims, 9 Drawing Sheets

(51) Int. Cl.
- *G01N 1/34* (2006.01)
- *G01N 1/40* (2006.01)
- *C07K 1/14* (2006.01)
- *C07K 1/36* (2006.01)
- *B01J 39/26* (2006.01)
- *B01J 41/20* (2006.01)
- *B01J 47/022* (2017.01)
- *B01J 47/014* (2017.01)
- *B01J 47/127* (2017.01)

(52) U.S. Cl.
 CPC ........... *B01J 47/022* (2013.01); *B01J 47/127* (2017.01); *B01L 3/505* (2013.01); *C07K 1/14* (2013.01); *C07K 1/36* (2013.01); *G01N 1/405* (2013.01); *B01L 2200/12* (2013.01); *B01L 2300/0681* (2013.01); *B01L 2300/123* (2013.01)

(56) References Cited

U.S. PATENT DOCUMENTS

| | | | |
|---|---|---|---|
| 5,695,989 A * | 12/1997 | Kalamasz | B01L 3/502 210/276 |
| 6,673,598 B1 | 1/2004 | Akers et al. | |
| 6,706,191 B1 | 3/2004 | Leijon | |
| 7,347,943 B2 | 3/2008 | Herman | |
| 2003/0111414 A1 * | 6/2003 | Baurmeister | B01D 61/007 210/641 |
| 2005/0256471 A1 | 11/2005 | Dibb et al. | |
| 2008/0249206 A1 | 10/2008 | Flohr et al. | |
| 2011/0198286 A1 | 8/2011 | Niazi | |
| 2012/0016113 A1 | 1/2012 | Niazi | |
| 2012/0018380 A1 | 1/2012 | Niazi | |
| 2012/0285328 A1 | 11/2012 | Kirtikar et al. | |
| 2012/0294826 A1 | 11/2012 | Spitalnik et al. | |

FOREIGN PATENT DOCUMENTS

| | | |
|---|---|---|
| CN | 101617072 A | 12/2009 |
| CN | 101868293 A | 10/2010 |
| JP | 2012-000241 A | 1/2012 |
| WO | 2001/97973 A1 | 12/2001 |
| WO | 2008/057426 A2 | 5/2008 |
| WO | 2009/045269 A1 | 4/2009 |
| WO | 2011/041508 A1 | 4/2011 |
| WO | 2012/154928 A1 | 11/2012 |
| WO | 2014/120344 A2 | 8/2014 |

OTHER PUBLICATIONS

International Search Report received for PCT Patent Application No. PCT/US2013/074857, dated Nov. 27, 2014, 3 pages.

European Application Serial No. 3874031.1, Extended European Search Report dated Aug. 19, 2016.

* cited by examiner

Figure 8A & B

DISPOSABLE DIRECT CAPTURE DEVICE

FIELD OF THE INVENTION

The embodiments disclosed herein relate to a flexible disposable sample preparation device containing an adsorptive functionalized fiber suitable for bind and elute purification of liquid samples containing biomolecules of interest.

BACKGROUND OF THE INVENTION

A number of methods for separating, purifying or preparing biological and/or chemical liquid samples currently exist. Fluidized bed chromatography, and separation medium filled chromatography columns have all been employed with varying success to separate and/or purify biological and/or chemical substances of interest from liquid samples with respect to yield, time consumption, purity and cost.

The primary template process for commercial harvest of monoclonal antibodies (mAbs) is to remove the visible (turbidity) cells and cell debris through a clarification train then loading directly onto a traditional bead based bind/elute capture chromatography column.

Clarification is typically a two step process. The first step is either depth filters or a disk-stack centrifuge. Currently fully disposable depth filter are not well suited to use with any current sterilization techniques. Using depth filters in stainless housings allows the use of steam for sterilization, but adds hardware and the need for cleaning and validation of the cleaning. Depth filters are limited in the cell density and total batch size where they are practical. The use of a disk-stack centrifuge takes away some of the performance limitations of depth filters for primary clarification, but brings with it many of its own challenges in cleaning, aseptic operation, and sealability. Secondary clarification is typically performed with depth filters with the same aseptic challenges as when used for primary clarification. The performance limitations for secondary primarily are where a large small particle concentration is present. A final membrane filter is typically employed to for bioburden reduction and to protect the chromatography steps downstream that could be easily fouled by remaining solids.

The ligand of choice for the chromatography step is typically Protein A with cation exchange used occasionally. The hardware required to pack and operate pilot scale and larger chromatography columns is significant, and requires careful packing and characterization. Because of the high cost of the resin and the effort required to pack it into an effective bed the columns are typically cleaned in place and re-used through a campaign or until the end of the resin life.

Current clarification methods struggle with achieving aseptic conditions (continuous centrifuge, disposable cellulosic depth filter devices). Steaming of cellulosic devices currently only safe in capital intensive stainless housings that subsequently require cleaning. Aseptic requirement more significant for vaccine harvest or gray space processing.

In addition current clarification methods struggle to clarify harvests with very high solids or high concentrations of small particulates, and have trouble achieving good yield with low titer harvests.

Recently, clarification methods have alternatively been carried out in installations in which the components in contact with the sample liquid are single-use components.

Such single-use components have the advantage of avoiding cleaning operations, but, to provide the required degree of security, the implementation of an installation with such components necessitates operations of selection, assembly and verification which are relatively complex.

Accordingly, it would be desirable to have process clarification methods and components for treating liquid biological samples and feeds that are convenient to implement, simpler, less expensive, and rely on single-use components that have low demands for bed properties by relying on static binding, and that do not require careful column packing and/or characterization the require specialized equipment and relatively expensive device designs.

SUMMARY OF THE INVENTION

The present invention is directed towards a flexible, collapsible, disposable two-dimensional or three-dimensional shaped device having an internal compartment defined by sidewalls, an interior surface, an exterior surface, an inlet for receiving liquid samples and feed containing a biomolecule of interest, an outlet for discharging the processed liquid samples and feed, and a high surface area adsorbent element contained within the internal compartment of the device having a first end and a second end, wherein either one or both ends are attached to interior surface of the device.

In certain embodiments, the present invention relates to a flexible, disposable device, such as bag or pouch, for purifying a biopharmaceutical liquid sample and/or feed in order to obtain biomolecule products such as vaccines, recombinant proteins, cells, stem cells, monoclonal antibodies (mAbs), proteins, antibodies, peptides, oligopeptides, nucleic acids, oligonucleotides, RNA, DNA, oligosaccharides and polysaccharides.

In certain embodiments of the present invention, the first end of the adsorbent element is securely fixed, bonded, or otherwise attached to the interior sidewall of the bag proximate the top periphery, and the send end of the adsorbent element is securely fixed, bonded, or otherwise attached to the interior sidewall of the bag proximate the bottom periphery of the bag.

In certain embodiments of the present invention the adsorbent element is a curtain or wall-like structure or other such configuration of polymeric fibers assembled substantially parallel to each other and fixed to the interior sidewall of the bag.

In certain embodiments of the present invention the adsorbent element is a curtain, or wall-like structure, or a bed of a shaped fiber(s), or other such configuration of polymeric fibers assembled substantially parallel to each other and substantially parallel to the longest dimensions of the bag, and fixed to opposing interior sidewalls of the bag proximate to and along the top periphery, and proximate to and along the bottom periphery of the bag.

In certain embodiments of the present invention the device is a collapsible polymeric bag, pouch, receptacle and the like.

In certain embodiments of the present invention the fibers are functionalized high surface area meltspun fibers.

In certain embodiments of the present invention, the device is well suited for low cost bind/elute purification especially from raw fluid streams containing high solids levels and or low protein concentrations (e.g. direct capture from cell harvest fluid or refold pools).

In other embodiments of the present invention, the parallel configuration of fibers along with the low initial quantity of fibers compared to fluid allows fluid containing solids such as cells and their debris to be introduced and contacted with the fibers with agitation without the solids becoming mechanically entrapped in the fiber matrix.

In still other embodiments, the invention provides a device supplied dry and pre-sterilized.

In one embodiment, body comprises a two-dimensional pillow-shaped bag wherein extruded or otherwise formed two polymeric sheets of material are placed in overlapping relation and the two sheets are bounded together at their peripheries to form an internal compartment. Alternatively, an extruded or otherwise formed single integral sheet of polymeric material can be folded over and seamed around the periphery to form internal compartment.

In still other embodiments, the bag is formed by initially extruding or otherwise forming a polymeric sheet in the form of a continuous tube, wherein the tube is cut to length and each end seamed closed to form a two-dimensional pillow style bag. In an alternative embodiment, each end can be folded like the end of paper bag, and then seamed closed so as to form a three dimension body.

In other embodiments of the present invention, the bag comprises a single integral sheet of extruded polymeric material which comprises two or more layer of different materials separated by a contact layer that are all simultaneously co-extruded.

In other embodiments of the present invention, the high surface area functionalized shaped fiber comprises adsorptive media for chromatography, particularly ion-exchange chromatography.

In other embodiments of the present invention, the functionalized shaped fiber contains a fibrillated, ridged or wing-shaped structure which greatly increases the surface area of the fibers.

In other embodiments, the present invention includes a method to add surface pendant functional groups to high surface area shaped fibers that provide cation-exchange or anion-exchange functionality. This pendant functionality is useful for the ion-exchange chromatographic purification of biomolecules, such as monoclonal antibodies (mAbs).

In other embodiments of the present invention, undesirable species and/or contaminants are removed from a sample fluid and feeds while maintaining the solids as the product (e.g. stem cell purification).

Additional features, aspects, and advantages of the invention will be set forth in the detailed description and claims, which follows. May modifications and variations of this invention can be made without departing from its spirit and scope, as will be apparent to those skilled in the art. It is to be understood that the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

DESCRIPTION OF THE EMBODIMENTS

Figure 1:
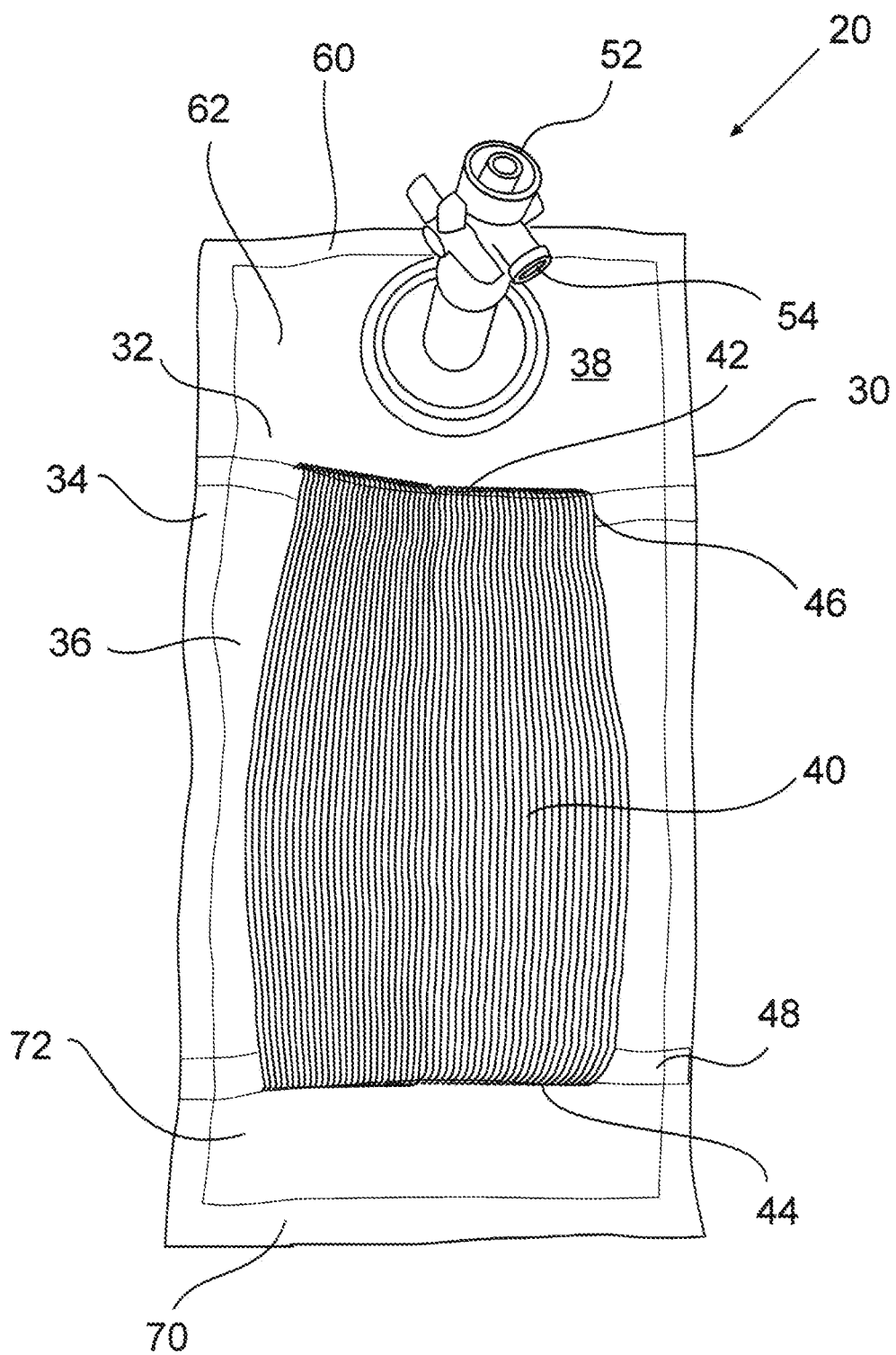
FIG. 1 is a photographic depiction of a liquid sample preparation device in accordance with certain embodiments.
Figure 2:
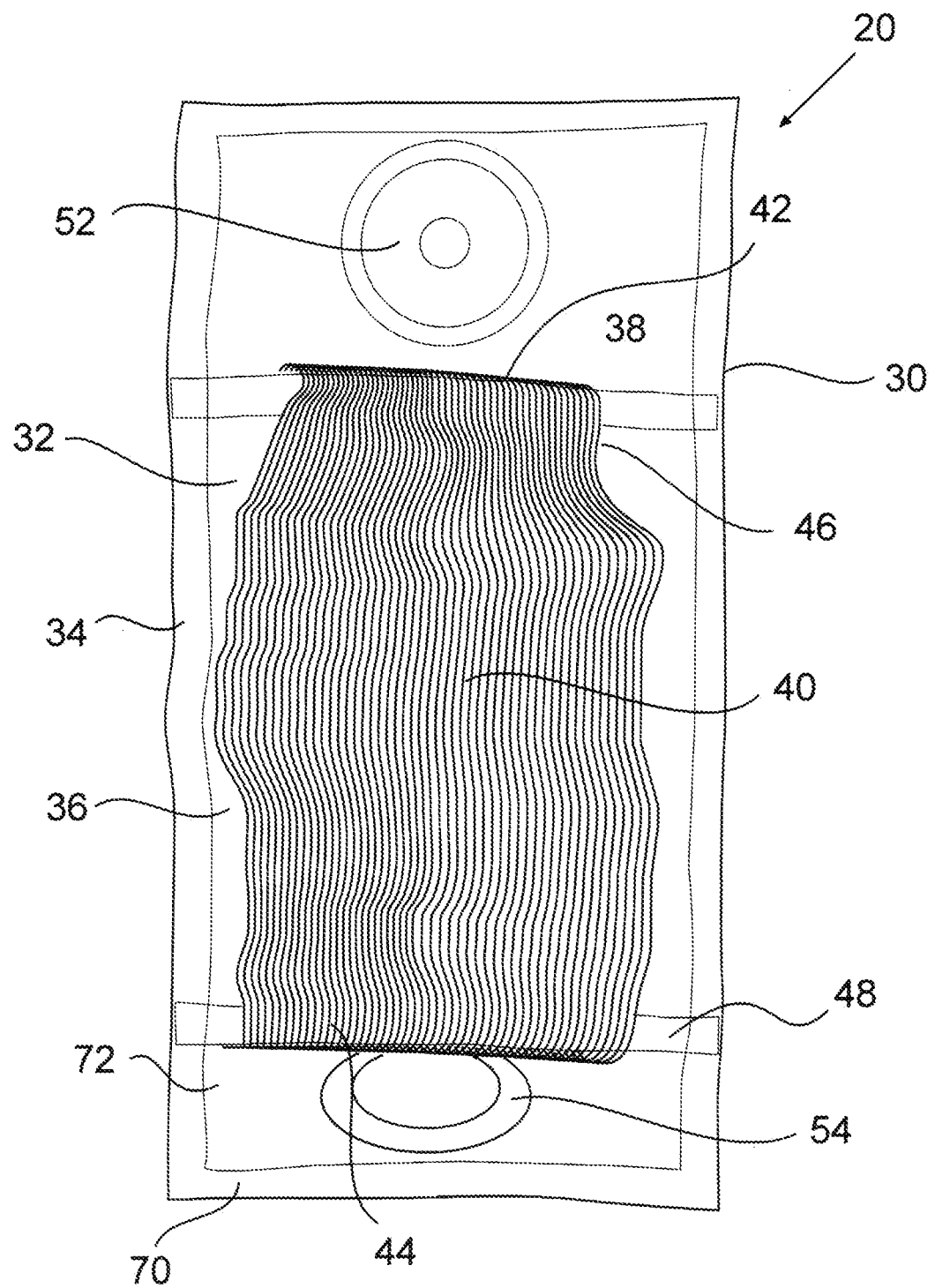
FIG. 2 is a photographic depiction of a liquid sample preparation device in accordance with certain other embodiments.
Figure 3:
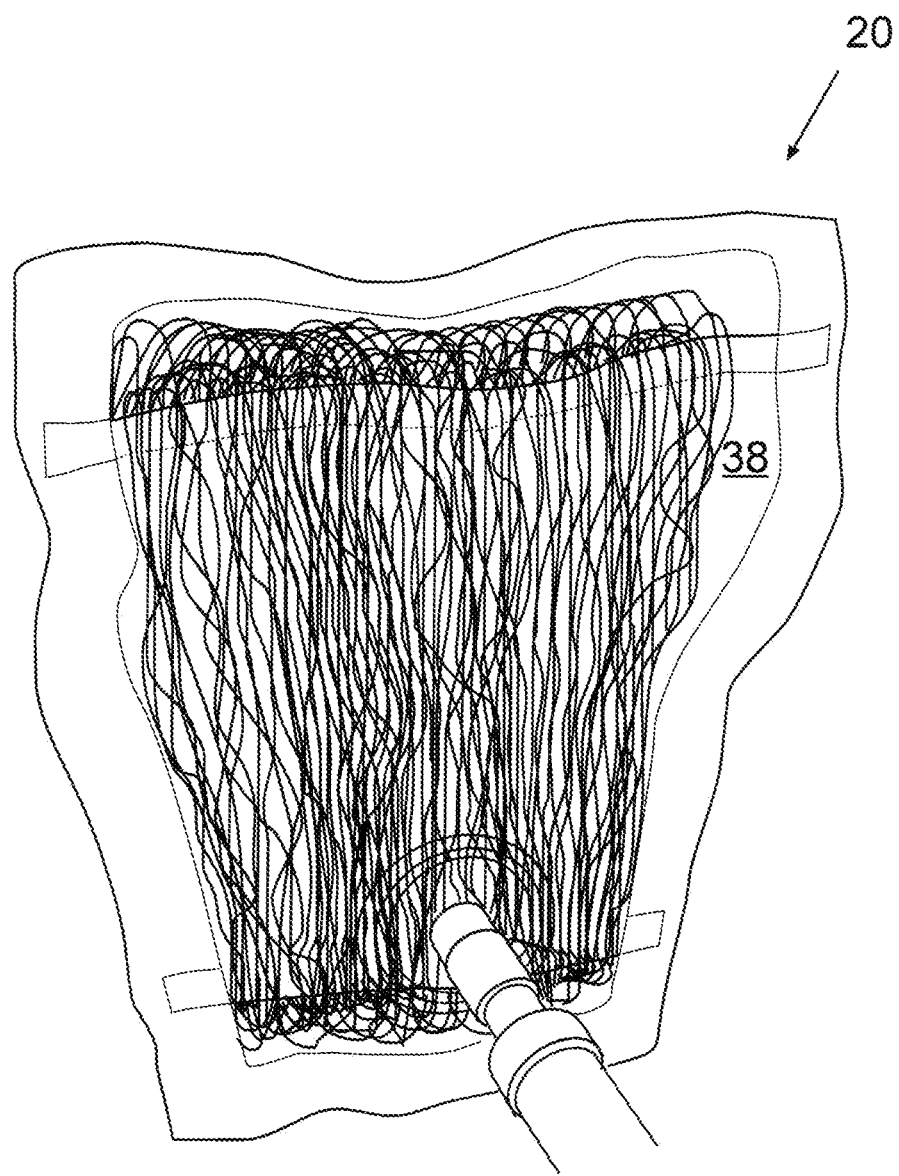
FIG. 3 is as photographic depiction of a liquid sample preparation device in containing a sample liquid in accordance with certain other embodiments.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein.

Shaped Fibers

The fiber may be in the form of a continuous length such as thread or monofilament of indeterminate length or they may be formed into shorter individual fibers such as nonwoven or woven fabrics, cutting the continuous length fiber into individual pieces, formed by a crystalline growth method and the like.

Preferably the fibers are made of thermoplastic polymers. The thermoplastic polymers include polyolefins, polypropylene, polyamide, sheathed polyethylene/polypropylene fibers, polysulfone, polyethersulfones, polyarylsulphones, polyphenylsulfones, polyvinyl chlorides liquid crystalline polymers, polyesters such as polyethylene terephthalate, including ultrahigh molecular weight polyethylenes, polybutylene terephthalate, copolyesters, and the like, and thermoplastic elastomers, polyvinylidene fluoride (PVDF) including, but not limited to, thermoplastic polyurethane elastomers (TPUs) such as polyethers, polyether esters, and PBAX and elastomeric olefins, and acrylates such as polymethylmethacrylate, styrenic polymers and mixtures of the above.

In certain embodiments, the fiber cross-section is generally winged-shaped, with a main body region defining a substantially longitudinal axis, and a plurality of protections extending radially outwardly from the main body region. The projections form an array of co-linear channels that extend along the length of the fiber, typically 20-30 such channels per fiber, and the length of the projections is shorter than the length of the main body region.

Suitable channel widths between projections range from about 200 nanometers to about 1000 nanometers. Suitable fibers are disclosed in Tanaka U.S. Pat. No. 6,811,874B2 to Tanaka et al, titled "Composite Fiber"; U.S. Patent Publication No, 2008/0105612, to Chappas, titled "Composite Filter Media With High Surface Area Fibers", and in U.S. Patent Publication No. 2012/0029176, to Yavorsky et al., titled "Chromatography Media And Method", wherein each of these disclosures are incorporated herein by reference.

The fibers can be wet or dry sterilized chromatographic medium. In a preferred aspect, the wet or dry chromatographic medium is sterile. The bag can be sterilized by treatment with radiation, autoclaving or chemical disinfectants. Gamma radiation is particularly effective. Milder treatments can also be used to reduce the microbial load, or total number of microbes such as bacteria and fungi present in the medium.

Functional Shaped Fibers

Chemical treatment methods to functionalize such fiber surfaces are provided to enable bio-molecular and biological separations based on adsorptive interaction(s). Chemical treatment method can impart a variety of surface chemical functionalities to such fibers based on ionic, affinity, or hydrophobic interactions or combinations of interactions. The combined economies of fiber production and simple surface chemical treatment processes yield an economical and readily scalable technology for purification operations in biopharmaceutical as well as vaccine production.

The surface functionalization of the high surface area shaped fibers can be accomplished by a two step process. As provided in U.S. Patent Publication No. 2012/0029176, to Yavorsky et al., suitable functionalization process is grafting polymerization. The functionalization begins with the attachment of pendant allyl groups to the nylon 6 fiber surface by treatment of the fibers with ally glycidyl ether in the presence of aqueous sodium hydroxide at 50° C. for 12 hours. The pendant allyl groups serve as anchoring sites on the fiber surface as attachment points for the pendant acrylamide polymer functionality. Conditions for the solution polymerization of acrylamide monomers are provided, and the pendant allyl groups on the fiber surface attach to the growing polymer chains in solution. Thus, the allyl-functionalized fibers are subsequently treated with an aqueous solution of 2-acrylimido-2-methyl-1-propane sulfonic acid, N,N-dimethylacrylimide and ammonium persulfate at 80° C. for 4 hours. Upon heating to 80° C., persulfate decomposition initiates it free radical polymerization of the acrylic monomers. Under these conditions, the pendant allyl groups on the fiber surface serve as attachment points for the pendant acrylic polymer functionality. In this way, the acrylic polymer is covalently attached to the fiber surface.

In certain embodiments, the acrylamide polymer may be prepared separately, and later applied to the nylon fibers as a surface coating. The resulting surface-coated fibers demonstrated comparable IgG binding capacities to the allyl grafted materials.

In accordance with certain embodiments, the functionalization begins with the deposition of a cross-linked coating of hydroxypropylacrylate (HPA) and N,N'-methylenebis (acrylamide) (MBAm) onto the surface of the high surface area fibers. This step provides as reactive hydroxylalkyl functionality for a subsequent ceric ion initiated redox polymerization of an acrylamide monomer.

The HPS/MBAm treated fibers are reacted with an aqueous solution of 2-acrylamido-2-methyl-1-propanesulfonic acid sodium salt, ammonium cerium(IV) nitrate, and $HNO_3$ at 35° C. under a nitrogen atmosphere. Under these conditions, cerium oxidation of the crosslinked hydroxylalkyl (hydroxypropylacrylate) functionality on the fiber surface generates free radicals on the fiber surface and initiates a surface grafting polymerization of the 2-acrylamido-2-methyl-1-propanesulfonic acid monomer. Under such conditions, the surface initiated polymerization process produces a polymeric "tentacle" of polymerized (2-acrylamido-2-methyl-1-propanesulfonic acid) monomer. In this way, the acrylamide polymer is covalently attached to the fiber surface. Such processes are known as grafting polymerizations.

The chemical groups (binding and/or ligand groups) responsible for attracting and holding the entities desired to be captured. Alternatively, the polymer possesses chemical groups that are easily modifiable to incorporate the binding groups. The coating or covering is permeable so that impurities can be captured into the depth of the coating or covering, increasing adsorptive capacity. The preferred polymer is a polymeric primary amine. Examples of suitable polymeric primary amines include polyallylamine, polyvinylamine, polybutylamine, polylysine, their copolymers with one another and with other polymers, as well as their respective protonated forms. Suitable copolymers include vinyl alcohol-co-vinylamine, acrylamide-co-allyamine, ethyleneglycol-co-allylamine, and allylamine-co-N-isopropylacrylamide. A coating or covering made from polyallylamine (and/or its protonated form, for example polyallylamine hydrochloride (PAH)) has been found to be particularly useful. PAA is commercially available (Nitto Boseki) in a number of molecular weights, usually in the range from 1,000 to 150,000, and all these can be used for creating a membrane sorber. PAA and PAH are readily soluble in water. The pH of aqueous solution of PAA is about 10-12, while that of PAH is 3-5. PAA and PAH may be used interchangeably, however the pH of the final solution must be monitored and if necessary adjusted to the value above 10 so that non-protonated amino groups are available for reaction with a cross-linker.

Structure of the Sample Preparation Device

FIGS. 1-6 depict a disposable flexible sample preparation device 20 comprising a flexible collapsible body 30 having an internal compartment 32 defined by the a non-porous side wall 34 and having an interior surface 36, an exterior surface 38, a first end 60 that terminates at a top periphery 62, a second end 70 that terminates at a bottom periphery 72, an inlet 52 for receiving liquid sample, and an outlet 54 for discharging treated liquid and a high surface area adsorbent polymeric element 40 contained within the internal compartment of the body, the adsorbent polymeric element having a first end 42 and a second end 44 wherein the first and second ends are attached to the interior surface of the body.

Body 30 of the device is comprised of a flexible, water impermeable, non-porous material such as polyethylene or other polymeric sheets having a thickness in a range between about 0.1 mm to about 5 mm with about 0.2 mm to about 2 mm being more common. Other thicknesses can also be used.

Figure 4:
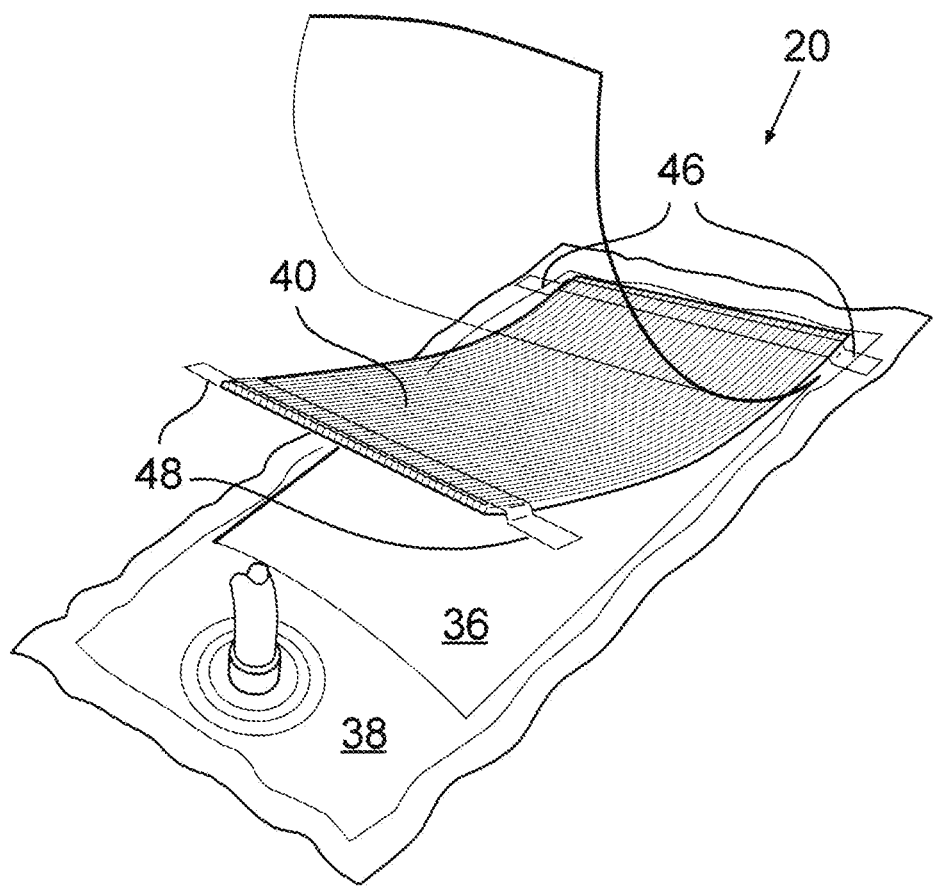
FIG. 4 is a cutaway photographic depiction of a liquid sample preparation device in containing a sample liquid in accordance with certain other embodiments.
Figure 5:
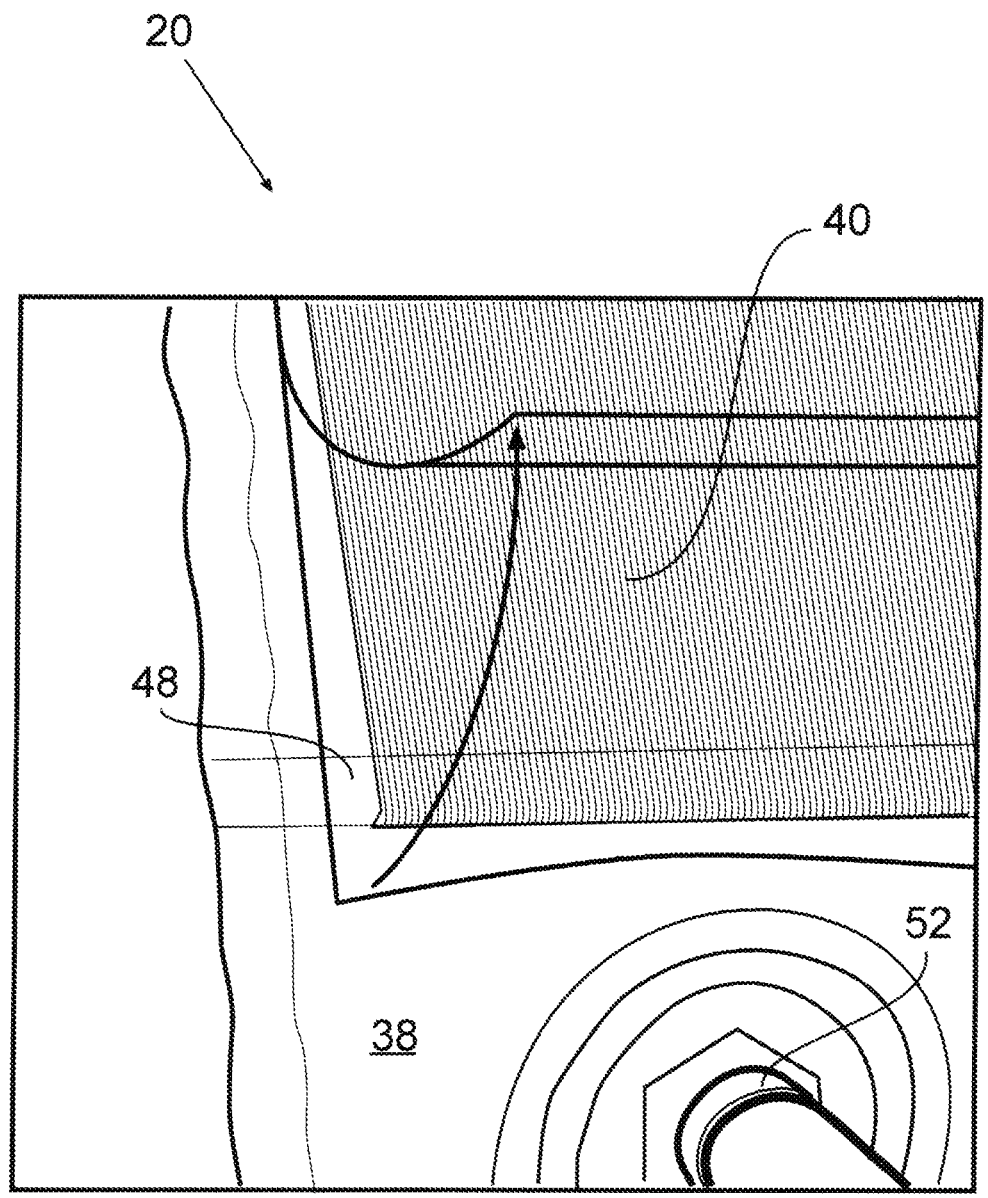
FIG. 5 is a cutaway photographic depiction of a liquid sample preparation device in containing a sample liquid in accordance with certain other embodiments.

FIGS. 4 and 5 depict cutaways of device 20, showing a certain embodiment as to how the high surface area adsorbent polymeric element 40 is fixed or otherwise bonded by way of an elongated polymeric strip 48 to opposing periphery sidewalls of bag 20.

Manufacture of the Sample Preparation Device

The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material can comprise a single integral sheet which comprises two or more layer of different material separated by a contact layer that are all simultaneously co-extruded.

In one embodiment, body 30 comprises a two-dimensional pillow-shaped bag wherein two sheets of material are placed in overlapping relation and the two sheets are bounded together in their peripheries to form an internal compartment 32. Alternatively, a single sheet of material can be folded over and seamed around the periphery to form internal compartment 32.

Although body 30 is depicted in FIGS. 1-6 as having a two-dimensional substantially pillow-shaped configuration, it is appreciated that body 30 can be manufactured to have virtually any desired size, shape, and configuration.

For example, body 30 can be formed having an internal compartment 32 sized to hold 100 ml, 500 ml, 1 liters, 10 liters, or other desired amounts. In any embodiment, however, it is desirable that the body 30 is received in an optional holder (not shown), providing at least generally uniform support of body 30 to preclude failure of body 30 by hydraulic forces applied to body when filled with liquid sample containing the biomolecules of interest.

A three-dimensional body (not shown) comprises a plurality, i.e., typically three or more, discrete panels. The body is comprised of four panels, i.e., top panel, front panel, back panel, and bottom panel. (not shown) Each panel preferably has a substantially square or rectangular central portion. Top panel and bottom panel include a first end portion and an opposing second end portion projecting from opposing ends of central portion. Each of end portions have a substantially trapezoidal configuration with opposing tapered edges. Front panel and back panel each include a triangular first end portion and an opposing triangular second end portion projecting from opposing ends of central portion. (not shown)

The corresponding perimeter edges of each panel are seamed together so as to form a substantially box shaped body. (not shown) Panels are seamed together using methods known in the art such as heat energies, RF energies, sonics, other sealing energies, adhesives, or other conventional processes. It is appreciated that by altering the size and configuration of some or all of panels, body can be formed having a variety of different sizes and configurations. It is also appreciated that any number of panels can be used to adjust the size and configuration of body.

In still another embodiment, a length of tube can be laid flat so as to form two opposing folded edges. The two folded edges are then inverted inward so as to form a pleat on each side. The opposing end of the tube are then seamed closed. Finally, an angled seam is formed across each corner so as to form a three dimensional bag when inflated.

It is appreciated that the above techniques can be mixed and matched with one or more polymeric sheets and that there are still a variety of other ways in which body can be formed having a two or three dimensional configuration.

Tubes and/or containers are then coupled (not shown) to at least one of ports 52 and 54 for delivering a solution and removing solution into internal compartment 32 of sample preparation bag assembly 20.

FIGS. 1-6 depict examples of the number and nature of ports the bag can have. One skilled in the art would know the requirements for a particular cell culture and could easily provide the necessary ports for a particular application.

Chromatography Systems

In some embodiments the invention provides a system for isolating, from a liquid samples and/or feeds, biomolecules of interest as the sample contacts the adsorptive curtain of functionalized shaped fibers. Liquid samples include unclarified liquid feed and samples containing one or more biomolecules of interest, including cells, stem cells, monoclonal antibodies (mAbs), proteins, antibody, peptides, oligopeptides, nucleic acids, oligonucleotides, RNA, DNA, oligosaccharides and polysaccharides.

In some embodiments the invention provides the system includes the device, a housing suitable for holding the device, one or more pumps and/or compression devices to facilitate flow of the mixture to and from the device.

Suitable pumps include peristaltic pumps, pulsed pumps and/or positive displacement pumps.

The system may include one or more means to detect the contents of an eluant from the adsorptive curtain of functionalized shaped fibers. The detector may be a light based detector which relies on multi-wavelength detection or single wavelength detection. Suitable detectors include a spectrophotometer capable of detecting visible wavelengths of light, a UV absorption detector, a fluorescence detector. The detector may be a light scattering detector which relies on a laser source or an electrochemical detector which responds to substances that are either oxidizable or reducible and the electrical output is an electron flow generated by a reaction that takes place at the surface of the electrodes.

The system may also include one or more printers for providing chromatograms of the eluted material from the chromatography media. The system may also include one or more personal computers. The personal computer may be suitable for recording data such as the absorbance or fluorescence of an elution fraction. Additionally the computer may be equipped with suitable software to calculate the concentration of a target molecules in an elution fraction.

Method of Use

In certain embodiments the invention provides devices, and methods for using and methods of making the devices, wherein once the functional shaped fibers have adsorbed the species of interest, the fluid including the remaining solids is emptied from the devices.

The invention may be used for filtering, separating, preparing, identifying, enriching, detecting, eluting, binding and/or purifying analytes, biomolecules, protein, mAbs, etc. of interest from liquid samples and feeds using the adsorbent polymeric curtain-like structure of one or more functionalized shaped fibers to bind/capture the species of interest, either the biomolecules of interest or contaminant particles (i.e., undesirable species) desired to be removed found in the liquid sample.

Alternative applications for the device include the removal of undesirable species from a fluid while maintaining the solids as the product (e.g. stem cell purification) to be collected in the permeate.

Figure 6:
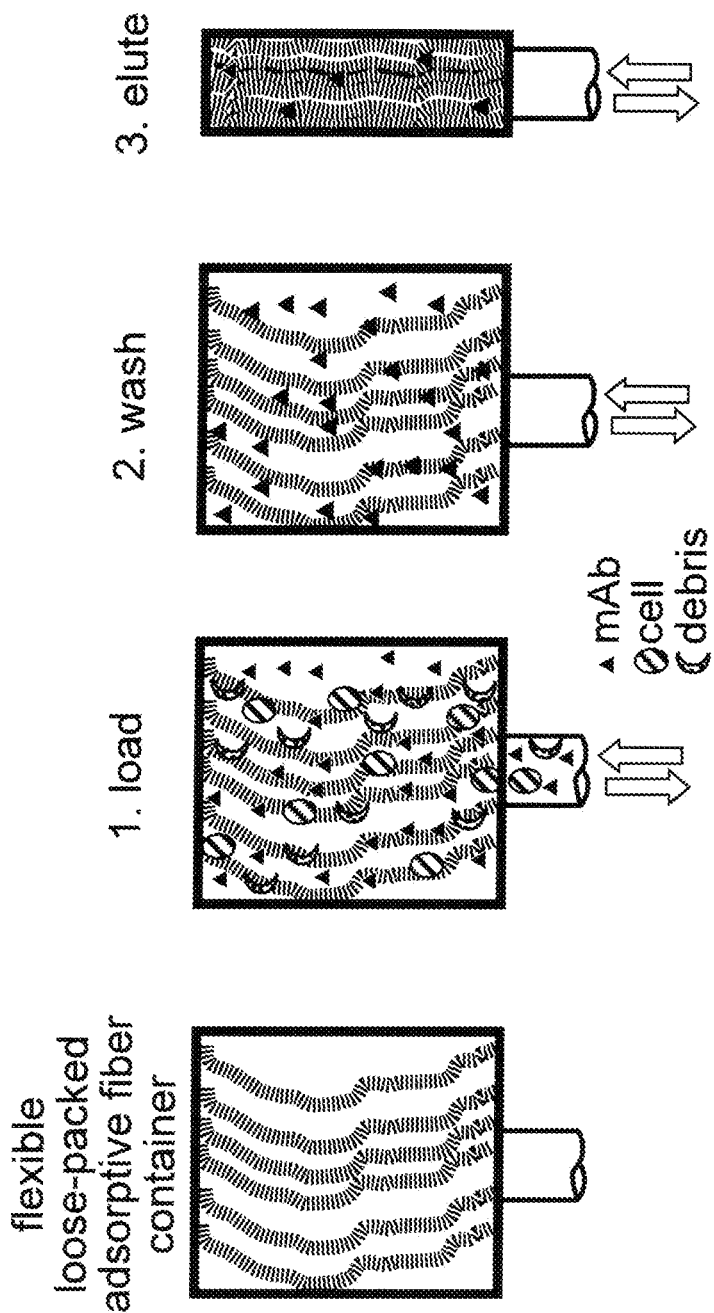
FIG. 6 depicts a schematic representation of loading, washing, and eluting a liquid sample preparation device in accordance with certain other embodiments.

FIG. 6 schematically depicts a certain embodiment for using the device 20.

The device 20 is loaded with raw unclarified feed containing slightly less protein then the capacity of the fibers for bonding is used.

Rinse/Wash: After agitating device 20 containing the liquid sample (See FIG. 3 which depicts a loaded bag 20) for some residence period of time, the device us emptied.

Possible methods for emptying the bag 20 include the use of gravity, a pump, vacuum, mechanical squeezing, etc., in order to efficiently empty the device and thereby minimize waste and maximize high concentration product recovery.

At each step where device 20 is emptied the maximum fluid removal efficiency is achieved by vacuum or other methods to compress the shaped fiber bed. The parallel configuration also aids in allowing high bed compression with minimal force resulting in efficient emptying and practical operation.

Of the many possible ways to activate the compression of the device a method that works from one end toward the exit port would keep the fiber bed minimally compressed during the majority of flow. For example the bag could be wound tight upon a rotating core with a pinch roller. (not shown)

Elute

Into empty bag device 20 add elute buffer (enough to fully wet).

Remove product saturate fluid and repeat several times to reach target recovery % without over diluting product.

Using a vacuum residual of 2 mL liquid/g fiber was achieved. Subsequent rinsing and elution steps operate with similar cycle steps. In practice for solids clearance the effective residual is about 10 mL liquid/g fiber.

Once the liquid sample is removed preparation bag 20, sample preparation bag can simply be discarded or recycled. A new sample preparation bag 20 is then used for a new batch of liquid samples. As a result, no tank or mixer cleaning is required between different batches and the risk of cross contamination is low.

In certain embodiments the invention includes a screen against the fiber bed that moves the liquid flow out of the fiber bed. (not shown)

EXAMPLE

Example 1

Solids Clearance Using Device 20

An experiment was performed to demonstrate clearance of solids such as cells/debris from a liquid sample using certain embodiments of the present invention.

Unmodified cell culture harvest was loaded into device 20 at 100 mL/g fiber and subsequently cycled with PBS buffer to represent washing and elution steps.

Turbidity was monitored at each step with 10 NTU being a reasonable challenge for a sterilizing grade membrane filter before sending the product downstream for further purification.

Figure 7:
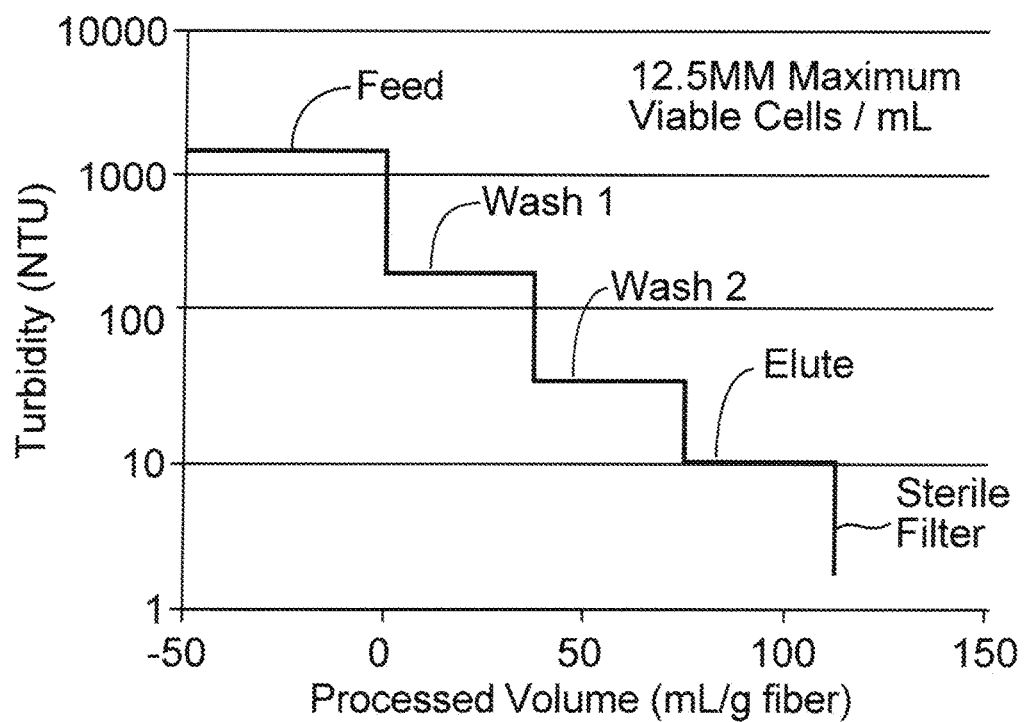
FIG. 7 is a graph showing turbidity vs. dilution of processed volume of liquid sample containing cells using the liquid sample preparation device in accordance with certain other embodiments.

By building a calibration curve for turbidity vs. dilution it was calculated that 99.5% of the solids by mass were removed before sterile filtration. (See FIG. 7)

Figure 8:
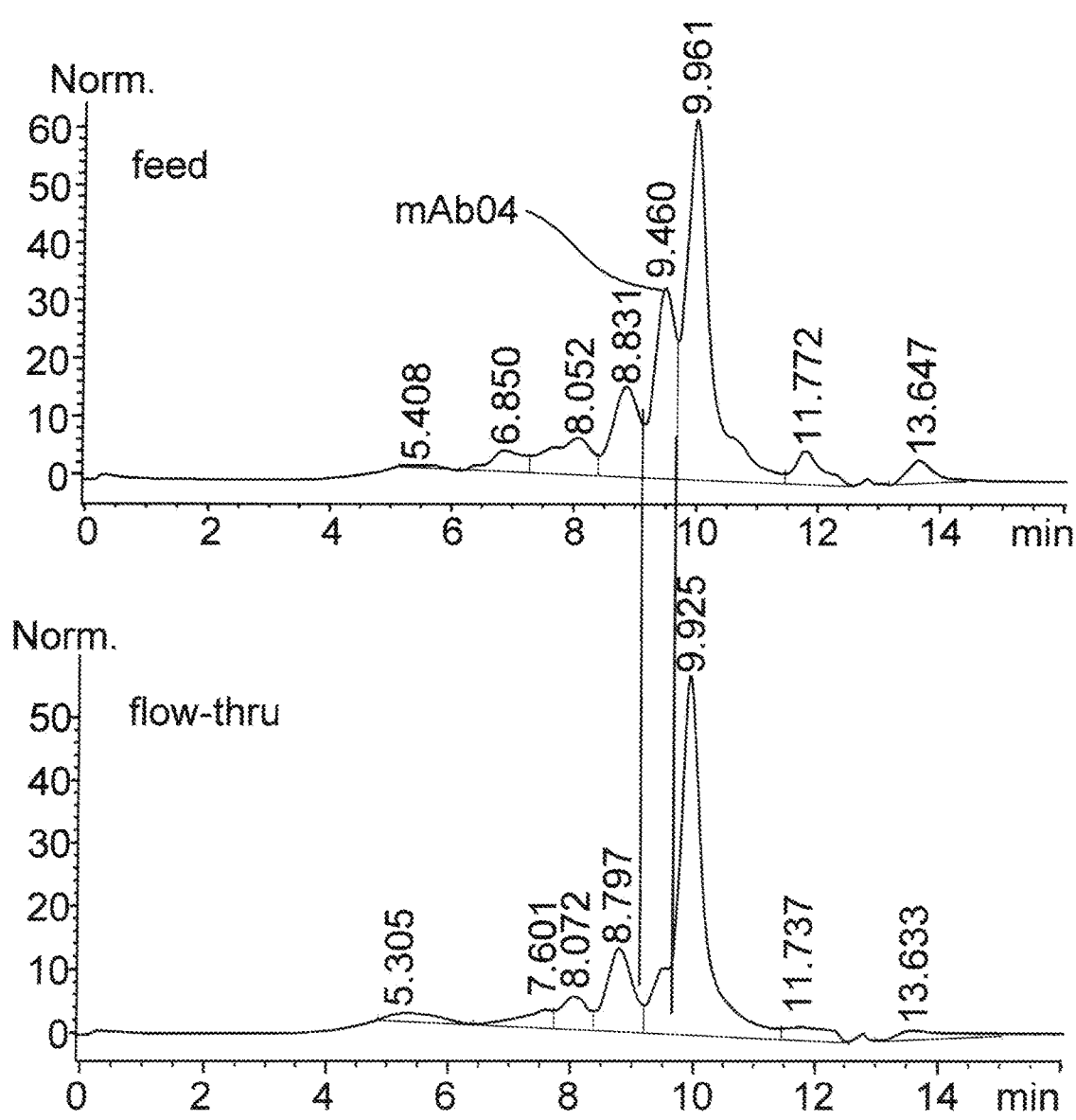
FIGS. 8A and 8B are plots of feed and flow-thru using the liquid sample preparation device in accordance with certain other embodiments.

Protein Separation Using Device 20 (See FIGS. 8A and 8B)

Using the same buffer volumes, a protein separation performed of a 20 mM MES+0.1M NaCl pH 6 buffer spiked with 0.17 mg/mL mAb04 and 1 mg/mL BSA.

The same buffer without protein was used for washing.

Figure 9:
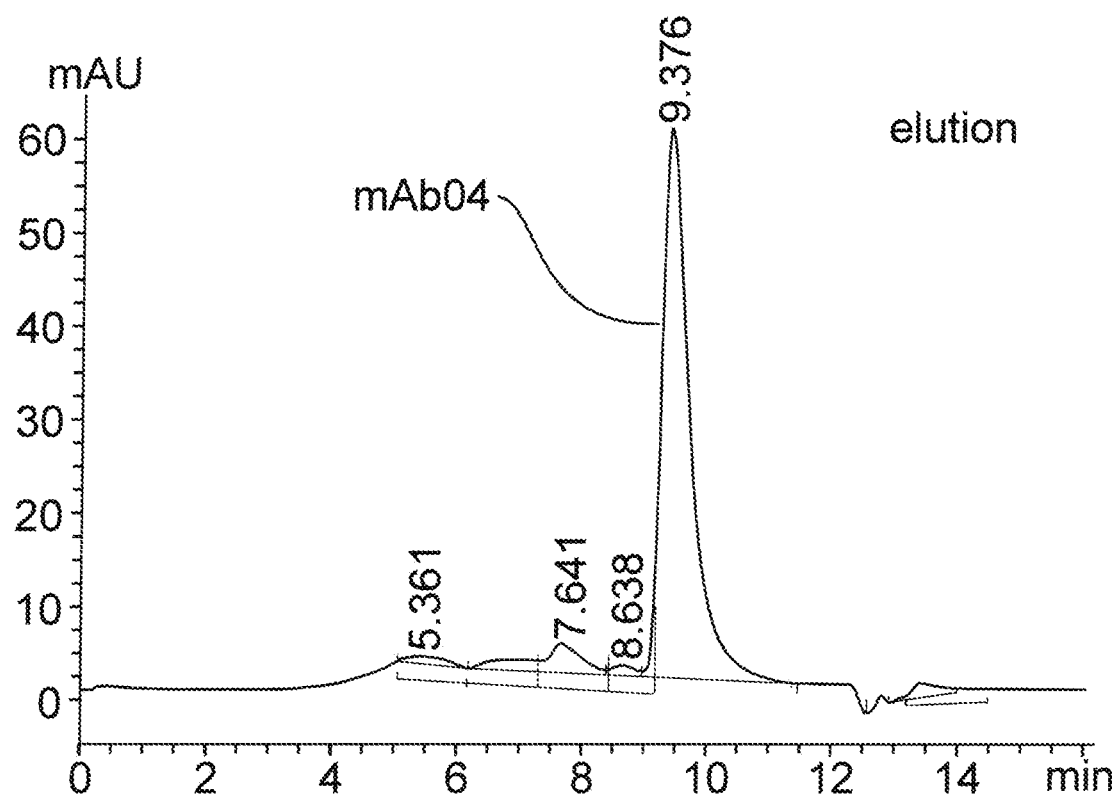
FIG. 9 is a plot of elution using the liquid sample preparation device in accordance with certain other embodiments.

The elution buffer was 20 mM MES+0.5M NaCl pH 6. (See FIG. 9)

Yield: >90% bound mAb recovered

Residual liquid (mAb) left in device=1%

Purity 3.7% of original BSA (0.09 mg/mL) in elution pool (LVR=1.2)

purification factor=5

Kits

The invention also provides kits which may be used to isolate, capture, purify or otherwise treat biomolecule analytes of interest from a liquid sample. The kit may comprise, for example, one or more bags having the adsorbent polymeric curtain-like structure of one or more shaped fibers therein according to the instant invention and one or more holders. The kit may contain one or more controls or sample analytes of interest and may optionally include various buffers useful in the methods of the invention. As an example the kit may include buffers, wash buffers for eliminating reagents or non-specifically retained or bound material may optionally be included in the kit. Other optional kit reagents include an elution buffer for eluting a bound target nucleic acid from the adsorbent polymeric curtain-like structure of one or more shaped fibers.

Each of the buffers may be provided in a separate container as a solution. Alternatively the buffers may be provided in dry form or as a powder and may be made up as a solution according to the user's desired application. In this case the buffers may be provided in packets. The kit may provide a power source in instances where the device is automated as well as a means of providing an external force such as a vacuum pump, compression devices and the like. The kit may also include instructions for using the device and/or loading the adsorbent polymeric curtain-like structure of one or more shaped fibers and/or for making up reagents suitable for use with the device and methods according to the instant invention. Optional software for recording and analyzing data obtained while practicing the methods of the invention or while using the device of the invention may also be included.

The term "kit" includes, for example, each of the components combined in a single package, the components individually packaged and sold together, or the components presented together in a catalog (e.g., on the same page or double-page spread in the catalog).

The invention will be further clarified by the following examples which are intended to be exemplary of the invention.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention, The disclosure set forth above may encompass multiple distinct inventions with independent utility. Although each of these inventions has been disclosed in its preferred embodiments, including the best mode known to the inventors for carrying out the invention the specific embodiments thereof as disclosed and illustrated herein are not to be considered in a limiting sense, because numerous variations are possible, and will become apparent to those of ordinary skill in the art upon reading the foregoing description. The inventors expect skilled artisans to employ such variations as appropriate, and the inventors intend for the invention to be practiced otherwise than as specifically described herein. The subject matter of the inventions includes all novel and nonobvious combinations and subcombinations of the various elements, features, functions, and/or properties disclosed herein. Accordingly, this invention includes all modifications and equivalents of the subject matter recited in the claims appended hereto as permitted by applicable law. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A disposable flexible liquid sample preparation device 20 comprising:
    a collapsible body 30 having an internal compartment 32 defined by sidewalls 34, an interior surface 36, an exterior surface 38, an inlet 52, an outlet 54, and an adsorbent polymeric element 40 contained within the internal compartment, the adsorbent polymeric element comprising a continuous, shaped monofilament fiber assembled in loops substantially parallel to each other each of the loops having a first end 42 and a second end 44 wherein the first end and the second end are attached to an adsorbent polymeric bonding element 46, 48, wherein the adsorbent polymeric bonding elements are attached to opposing peripheries of the internal compartment.

2. The device of claim 1, wherein the body is a bag.

3. The device of claim 1, wherein the adsorbent polymeric element comprises a polymeric shaped fiber bed.

4. The device of claim 3, wherein the shaped fiber further comprises surface pendant functional groups that provide cation-exchange or anion-exchange functionality.

5. The device of claim 3, wherein the shaped fiber is meltspun.

6. The device of claim 3, wherein the shaped fiber has a cross-section with a middle region comprising a longitudinal axis that runs down the center of the fiber and having a plurality of projections that extend radially outwardly from the from the middle region.

7. The device of claim 3, wherein the shaped fiber comprises polyolefins, thermoplastic polymers, polypropylene, polyester, polyethylene, polyamide, copolyesters, liquid crystalline polymers, thermoplastic elastomers, thermoplastic polyurethane elastomers polyethers, polyether esters, PBAX elastomeric olefins or mixtures thereof.

8. A method of making a disposable flexible liquid sample preparation device (20) comprising:
    a) providing two polymeric sheets, each sheet having an outer periphery;
    b) providing an adsorbent polymeric element (40) comprising a continuous, shaped monofilament fiber, assembled in loops substantially parallel to each other, each of the loops having a first end 42 and a second end 44 wherein the first end and the second end are attached to at least one adsorbent polymeric bonding element (46 or 48), the bonding element having first and second ends;
    c) placing the adsorbent polymeric element and bonding element between the two polymeric sheets such that the outer peripheries of the two sheets overlap each other and the first and second ends of the bonding element are sandwiched between opposing overlapping outer peripheries;
    d) bonding together the two polymeric sheets at the overlapping outer peripheries and the first and second ends of the bonding element forming a device having an internal compartment for housing the adsorbent polymeric element fixedly attached to opposing outer peripheries of the two polymeric sheets.

9. The method of claim 8, wherein an outlet and an inlet are fixedly attached to the device.

10. A method of making a disposable flexible liquid sample preparation device comprising:
    a) providing a single polymeric sheet having an outer periphery;
    b) providing an adsorbent polymeric element comprising a continuous, shaped monofilament fiber, assembled in loops substantially parallel to each other, each of the loops having a first end and a second end, wherein the first end and the second end are attached to at least one adsorbent polymeric bonding element, the bonding element having first and second ends;
    c) placing the adsorbent polymeric element and bonding element on the polymeric sheet;
    d) folding the polymeric sheet such the outer periphery of the sheet overlap and the first and second ends of the bonding element are sandwiched between opposing overlapping outer peripheries;
    e) bonding the polymeric sheet at the overlapping outer periphery and the first and second ends of the bonding element;
    f) forming a device having an internal compartment for housing the adsorbent polymeric element fixedly attached to opposing outer peripheries of the polymeric sheet.

11. The method of claim 10, wherein an outlet and an inlet are fixedly attached to the device.

* * * * *